United States Patent [19]

Haber et al.

[11] Patent Number: 5,536,253
[45] Date of Patent: Jul. 16, 1996

[54] PRE-FILLED SAFETY SYRINGE HAVING A RETRACTABLE NEEDLE

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 275,955

[22] Filed: Jul. 15, 1994

[51] Int. Cl.$^6$ .............................. A61M 5/50; A61M 5/32
[52] U.S. Cl. ............................................ 604/110; 604/195
[58] Field of Search .................................... 604/110, 192, 604/195, 196, 228, 263

[56] References Cited

U.S. PATENT DOCUMENTS

| 2,879,766 | 3/1959 | Wilburn | 604/228 X |
|---|---|---|---|
| 4,192,919 | 3/1980 | Raghavachavi | 435/292 |
| 4,459,997 | 7/1984 | Sarstedt | 604/228 X |
| 4,808,169 | 2/1989 | Haber et al. | 604/195 |
| 4,908,022 | 3/1990 | Haber | 604/195 |
| 4,909,794 | 3/1990 | Haber et al. | 604/195 |
| 4,931,040 | 6/1990 | Haber et al. | 604/110 |
| 5,032,114 | 7/1991 | Olovson | 604/110 |
| 5,098,382 | 3/1992 | Haber et al. | 604/110 |
| 5,188,601 | 2/1993 | King | 604/110 |
| 5,267,962 | 12/1993 | Jenson | 604/110 |
| 5,328,484 | 7/1994 | Somers et al. | 604/195 |
| 5,330,440 | 7/1994 | Stanners et al. | 604/195 |
| 5,380,286 | 1/1995 | van den Haak | 604/110 |
| 5,408,326 | 4/1995 | Haber et al. | 604/110 |

Primary Examiner—John D. Yasko
Assistant Examiner—Adam J. Cermak
Attorney, Agent, or Firm—Hawes & Fischer

[57] ABSTRACT

The syringe of the present invention is ideally supplied to the user in a pre-filled state, with the piston stem protruding from the syringe body and with the cannula covered with a protective cover. Once the disposable safety syringe of the present invention is unwrapped, it may be used for performing an injection in the usual way. As the last bit of fluid is injected through the cannula, the piston engages the proximal portion of the needle axial translating structure. The piston stem is then withdrawn back through the syringe body, pulling the cannula inside the syringe body. The piston is prevented from exiting the syringe body because of the presence of a flange at the proximal end of the syringe. The piston stem is then quickly removable from the piston by disengaging the large-pitch thread with which it was attached to the piston, which eliminates the possibility of inadvertent proximal motion of the piston.

17 Claims, 3 Drawing Sheets

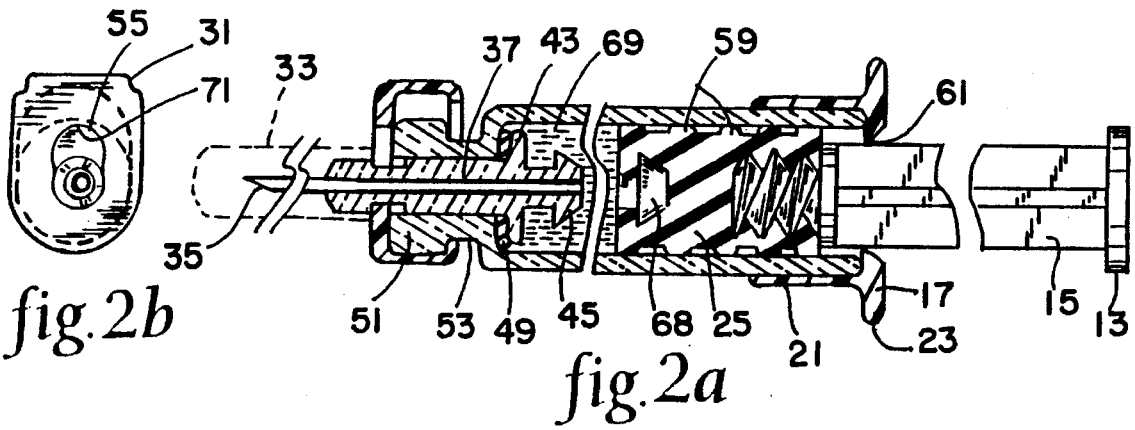
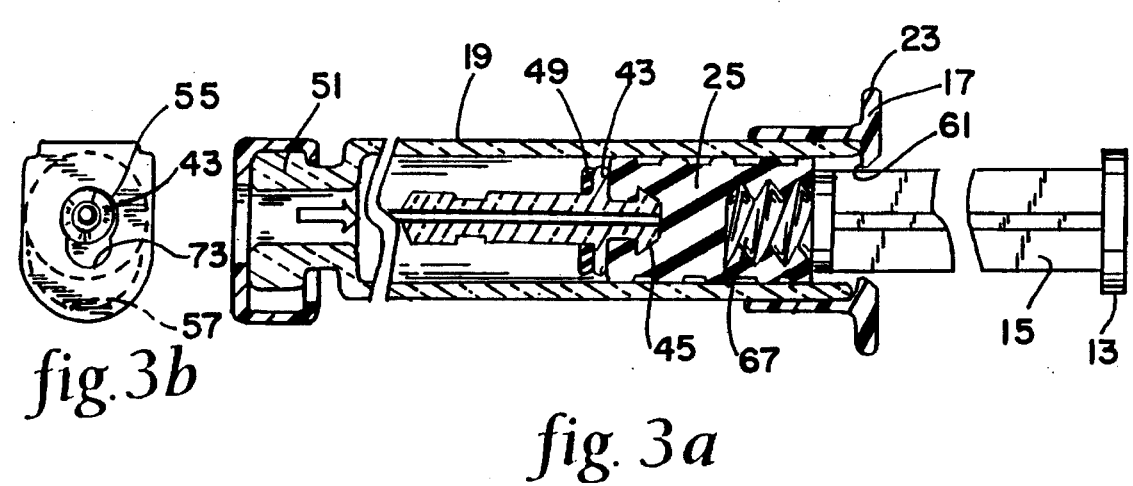
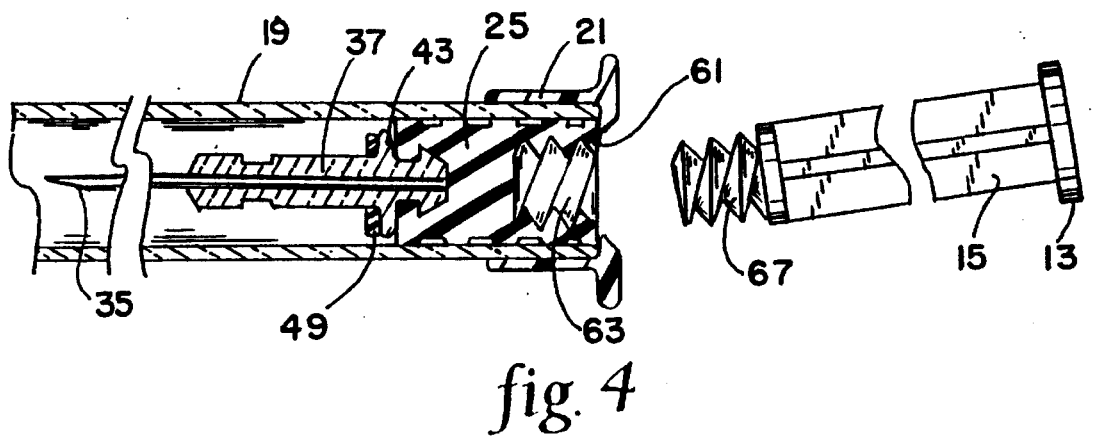

PRE-FILLED SAFETY SYRINGE HAVING A RETRACTABLE NEEDLE

FIELD OF THE INVENTION

The present invention relates to the medical device disposables field, and more specifically, to a unitary safety syringe which is a disposable, pre-filled syringe.

BACKGROUND OF THE INVENTION

Syringes which can prevent or reduce the probably of contaminated infection are in high demand, and those syringes which can offer a utility of operation which approaches or exceeds that of a non-safety syringe are in even higher demand. Some of the safety syringes which are known include U.S. Pat. No. 4,710,170, issued on Dec. 1, 1987 and entitled "Anti-Needle Strike and Anti-Drug Abuse Syringe" enabled the cannula to be withdrawn into the cylinder, and compressibly destroyed with the stem. U.S. Pat. Nos. 4,770,655 and 4,804,370, issued on Sep. 13, 1988 and Feb. 14, 1989 respectively and both entitled "Disease Control Syringe Having a Retractable Needle" enabled the cannula to be withdrawn into the cylinder, automatically canted to one side, and compressibly destroyed. All of the above mentioned syringes were invented by Terry M. Haber, William H. Smedley, and Clark B. Foster, the inventors of the present application.

One of the later designs includes U.S. Pat. No. 4,931,040, issued on Jun. 5, 1990 and entitled "Safety Syringe Having a Combination Needle Cannula and Articulating Hub for Retracting said Cannula into a Medication Carpule," and also issued to the inventors of the present application. In that invention a separate safety syringe was designed to accept a disposable, pre-filled capsule which was commercially known under the name CARPULE. The safety syringe could be used with any number of pre-filled capsules.

The disadvantages of that design includes a factor relating to the separability of the safety syringe from the capsules. One might be present, with the need to search for the other. Further, any re-usable structure raises concerns relating to sterility and cleanliness. When used in the surgical theater, a single drop from tainted blood could become lodged on a surface of the safety syringe to be later ejected onto another patient. Sterilization was also an issue. Where plastic was chosen for the safety syringe, continual re-sterilization could cause breakdown of materials or weakening of the material structure.

In the structures disclosed in the U.S. Pat. No. 4,931,040 the user would be required to load in a fresh capsule, use the syringe, retract the cannula and remove the capsule and load in a new capsule. The time required was slight, but in emergency room use, seconds are valuable. When action is required, the limitation of waiting until an old capsule can be removed and a new one loaded can be severe.

What is needed is a completely disposable syringe which is available in a pre-loaded condition and which can be used immediately by medical personnel. The cannula should be withdrawable at the leisure of the user, and the withdrawing action should be as brief as possible. The withdrawal procedure should render the syringe totally unusable, and safe disposal should be facilitated.

SUMMARY OF THE INVENTION

The pre-filled safety syringe having a retractable needle, of the present invention is a unitary, disposable syringe in which the needle cannula is retractable within the syringe body, and includes a removable piston stem to insure that the piston is not moved forward and that the syringe of the present invention can be safely disposed of in an acceptable container.

The syringe of the present invention is ideally supplied to the user in a pre-filled state, with the piston step protruding from the syringe body and with the cannula covered with a protective cover. Once the disposable safety syringe of the present invention is unwrapped, it may be used for performing an injection in the usual way. As the last bit of fluid is injected through the cannula, the piston engages the proximal portion of the needle hub. The piston stem is then withdrawn back through the syringe body, pulling the cannula inside the syringe body. The piston is prevented from exiting the syringe body because of the presence of a flange at the proximal end of the syringe. The piston stem is then quickly removable from the piston by disengaging the large-pitch thread with which it was attached to the piston, which eliminates the possibility of inadvertent proximal motion of the piston.

BRIEF DESCRIPTION OF THE DRAWINGS

The invention, its configuration, construction, and operation will be best further described in the following detailed description, taken in conjunction with the accompanying drawings in which:

FIG. 2a is a side sectional view illustrating the disposable safety syringe configured to deliver a liquid by operation of the piston stem and piston in the distal direction;

FIG. 2b is a front view which illustrates the slide lock mechanism of the disposable safety syringe of the present invention in a first position securing the needle and needle hub in place with respect to the syringe body;

FIG. 3a is a side sectional view illustrating the disposable safety syringe configured to withdraw the needle and needle hub by operation of the piston stem and piston in the proximal direction;

FIG. 3b illustrates the slide lock mechanism of the disposable safety syringe of the present invention in a second position having released the needle and needle hub to be withdrawn inside the syringe body; and FIG. 4 the illustrates the maximum rearward motion of the piston as it engages a radially inward lip attached to the syringe body, and further illustrates the threaded quick release of the piston stem from the piston which will prevent significant motion from being imparted to the piston in the distal direction.

DETAILED DESCRIPTION OF THE PREFERRED EMBODIMENT

Figure 1:
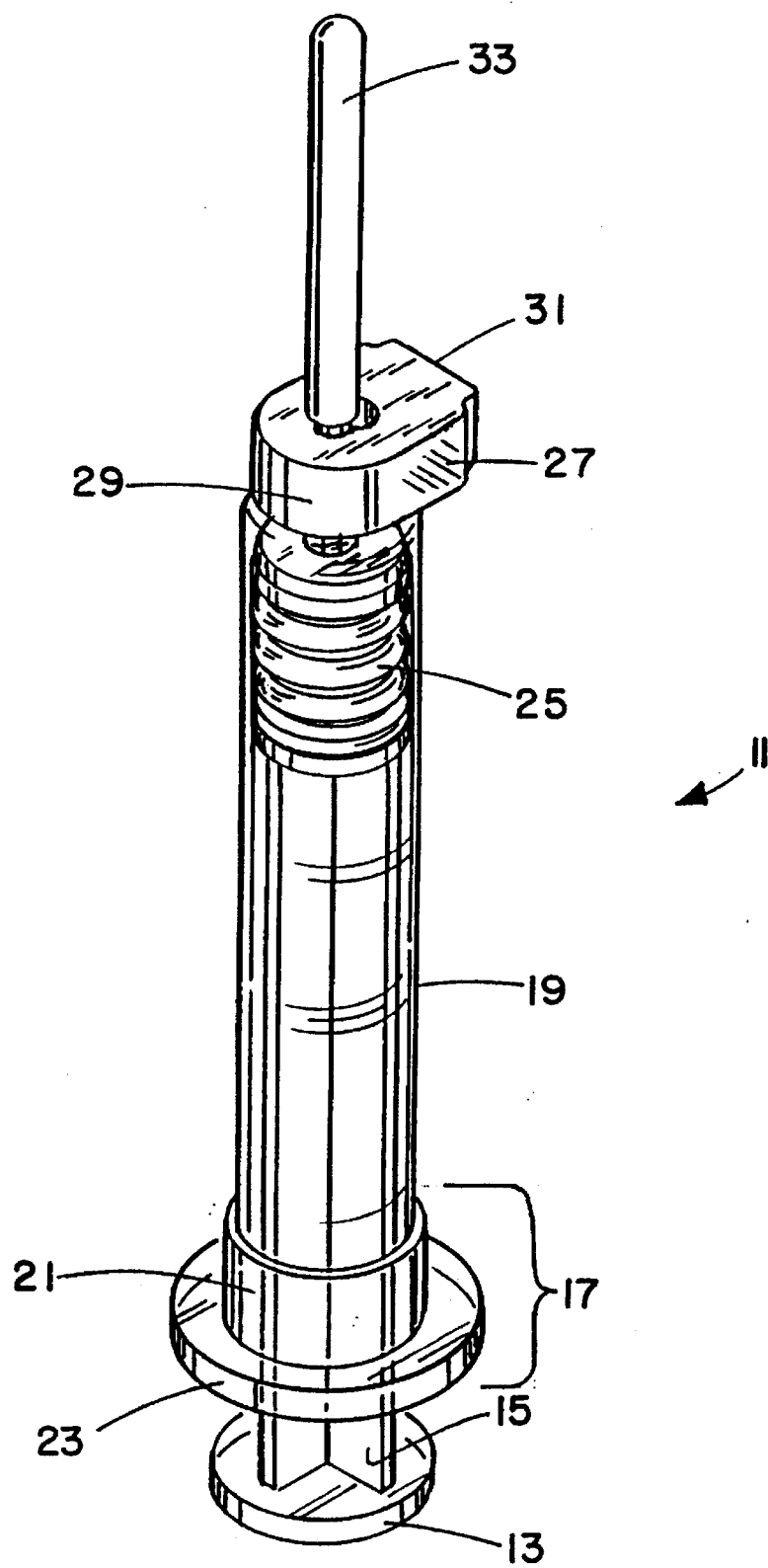
FIG. 1 is a side perspective view of the disposable safety syringe of the present invention as it would appear after having just been used.

The description and operation of the invention will be best described with reference to FIG. 1. FIG. 1 illustrates a perspective view of a disposable pre-filled safety syringe 11. Beginning at the proximal end, shown at the bottom of FIG. 1, a circular planar thumb plate 13 engages a piston stem 15. Piston stem 15 extends beyond a flange 17, and into a syringe body 19. Syringe body 19 is preferably a pre-filled syringe body 19. The flange 17 is rigidly affixed to the syringe body 19, and includes a concentrically smaller diameter portion 21 having a relatively longer axial length, and a relatively larger diameter portion 23 having a relatively shorter axial length.

The longer axial length of smaller diameter portion 21 is for the purpose of providing more area for a more secure rigid attachment to syringe body 19. Flange 17 may be bonded to the syringe body 19, but it preferably has a snap fit engagement. Syringe body 19 is cylindrically shaped and preferably made from a clear material. Syringe body 19 can be made from a low alkaline glass, type 1 borosilicate glass, commercially available CZ type resins, or a commercially available BAREX type thermoplastic resin, to name a few.

Since syringe body 19 is clear, the piston stem 15 is seen as connected to a piston 25. Just above piston 25 and connected to the syringe body 19 is a slide lock 27. Slide lock 27 has a curved surface 29, which generally conforms with the curvature of the syringe body 19, and a flat surface 31. The curved surface 29 can be used in conjunction with a curved bottom shipping container in which disposable pre-filled safety syringe can be placed evenly only so long as the slide lock 27 is not shifted from a position in which the disposable pre-filled safety syringe is ready for use.

At the most distal extent of the disposable pre-filled safety syringe is a cannula guard 33, which may be threadably engaged to another structure (not yet shown). Note that larger diameter portion 23 is significantly larger than smaller diameter portion 21 which will enable the index and middle finger to engage larger diameter portion 23 during the time when an injection is taking place to provide a force reference point against which thumb plate 13 can be depressed.

Figure 2:
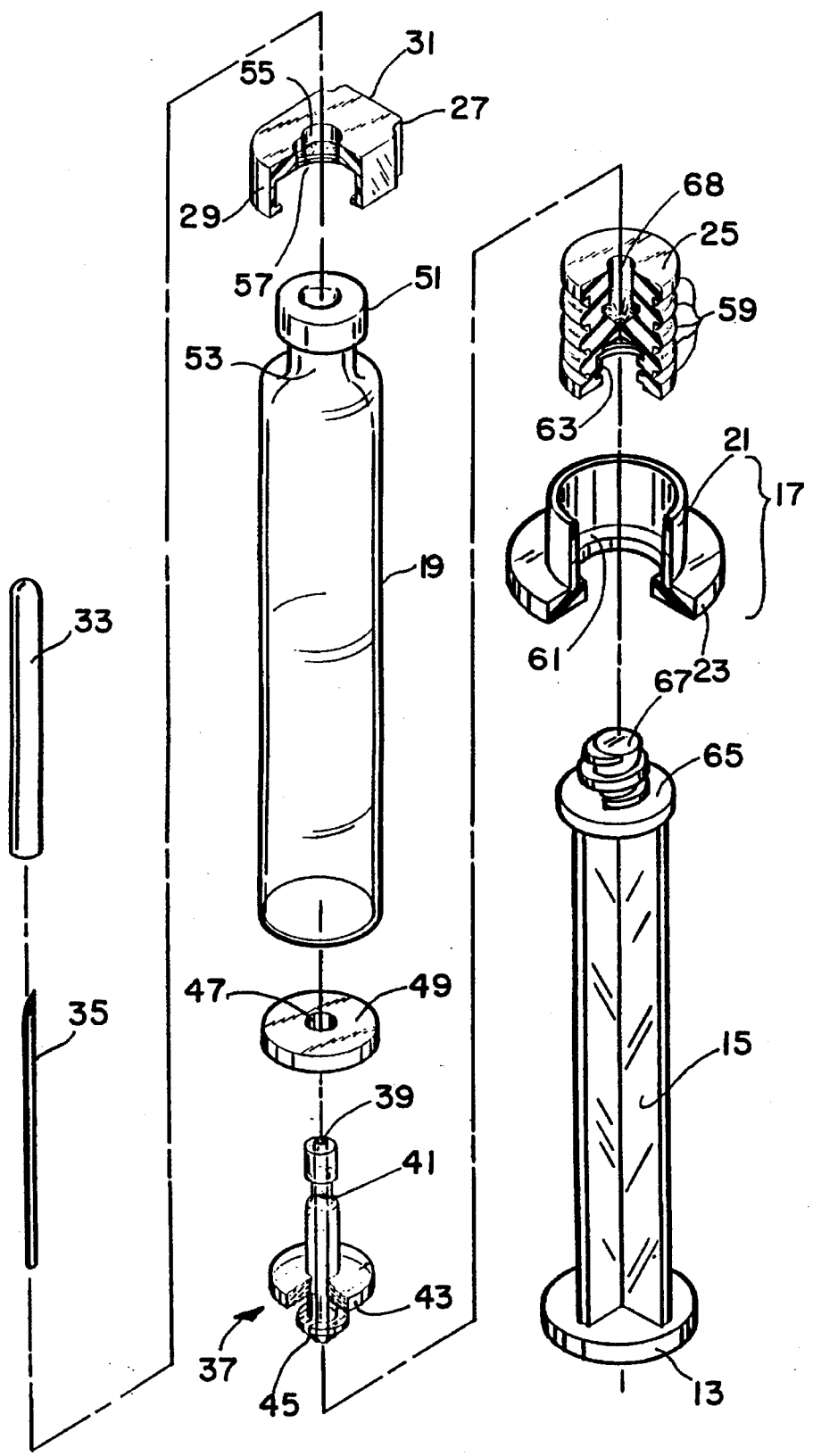
FIG. 2 is an exploded view, compressed in a serpentine manner and illustrating the component parts of the disposable safety syringe of the present invention.

Referring to FIG. 2, further details of the disposable pre-filled safety syringe are seen. Cannula guard 33 is seen covering a hypodermic needle, or cannula 35. The cannula 35 is rigidly attached to a needle axial translating structure 37 at its distal end. Needle axial translating structure 37 may include a small amount of epoxy in an epoxy joint 39 at the extreme distal end of needle axial translating structure 37. Needle axial translating structure 37 is also shown with other structures present including a peripheral groove or locking neck 41, and disk-like flange 43. Also shown at the proximal end of needle axial translating structure 37 is a stopper attachment cone 45. The distal end of needle axial translating structure 37 extends through an aperture 47 of a gasket 49.

The syringe body 19 has a distal end which includes a distal head 51 which is a flattened toroidal structure forming a neck 53 between distal head 51 and syringe body 19. Situated above the distal head 51 is the slide lock 27 which is shown in partially broken away fashion. The slide lock 27 has a pair of superposed apertures, including a smaller superposed aperture 55 and a larger superposed aperture 57. Smaller superposed aperture 55 is actually formed by the intersection of a smaller aperture with a larger aperture. The smaller aperture of smaller superposed aperture 55 is of a size to engage the peripheral locking neck 41 at least over a portion of its surface. The larger aperture of smaller superposed aperture 55 is sufficiently large that the distal end of needle axial translating structure 37 may pass through it. It is slide lock 27 which engages the needle axial translating structure 37 to hold it in place.

Larger superposed aperture 57 is actually formed by the intersection of two apertures of about the same size, but which have radial centers which are offset. The offsetting of the apertures of the larger superposed aperture 57 form a slight inward dip of the periphery of the larger superposed aperture 57 to act as a position delimiter. The size of the apertures of the larger superposed aperture 57 are intended to somewhat closely engage neck 53. In this manner, the slide lock 27 can be laterally snapped between two positions with respect to neck 53. In a first position, the smaller of the apertures of smaller superposed aperture 55 engages the needle axial translating structure 37, while in the second position, the larger of the apertures of smaller superposed aperture 55 disengages the needle axial translating structure 37. The distal head 51 serves to make sure that the slide lock 27 stays atop the distal head 51, regardless of which of the apertures of the larger superposed aperture 57 are occupied by the neck 53.

At the upper right of FIG. 2 is shown the piston 25, having a series of ribs 59 for sealable wiping engagement with respect to the inside of syringe body 19 to insure a good hydraulic seal and to insure that sufficient pressure for the liquid can be developed to deliver the liquid within the syringe body 19 without leaking around piston 25.

Further details of the flange 17 are shown, including the presence of a radially inwardly projecting lip 61. Lip 61 is made to insure that it will engage not only the proximal end of the syringe body 19, but that it will have an additional radially inwardly extending projection that will engage the proximal end of the piston 25 to insure that it will not be removable from the syringe body 19 once the piston 25 is within the syringe body 19 and the piston 25 is attached to the syringe body 19.

Also shown with regard to piston 25 is an internal threaded surface 63. The distal end of piston stem 15 terminates in a planar surface 65 supporting a large pitch thread 67. The large pitch of large pitch thread 67 enables it to be engaged with the matching internal threaded surface 63 with only a few relative turns. Note also the presence of a receptacle 68 in the distal end of piston 25. The receptacle 68 is sized to interfit with and interlock with the stopper attachment cone 45 of the needle axial translating structure 37.

Referring to FIGS. 2a–4, there are several views which illustrate the action of the disposable pre-filled safety syringe of the present invention. The sectional view of FIG. 2a illustrates a liquid 69, preferably a medicine to be delivered, which exists between the needle axial translating structure 37 and the piston 25. Note that the needle axial translating structure 37 is at rest at the distal end of the syringe body 19, and that gasket 49 is shown engaging the inner surface of the neck 53. With this sealing connection, the liquid 69 has nowhere to go except through the cannula 35 which is shown extending through the needle axial translating structure 37.

Note that, shown in the assembled configuration, the lip 61 extends to enough of a concentric extent to overlap the radially outward extent of the bottom of the piston 25. As can be clearly seen, lip 61 will act to prevent the proximal extent of travel of piston 25. This is an important feature when the disposable pre-filled safety syringe of the present invention is being filled, because a pressure sensor can be used to sense when the disposable pre-filled safety syringe is full., As the disposable pre-filled safety syringe, and more specifically the syringe body 19 is being filled, the piston 25 will move proximally until it reaches its fullest proximal extent. Thereafter, the pressure of the liquid 69 will rise, and can be used as an indicator to cease the filling of the syringe body 19.

Note also the engagement of the large pitch thread 67 with the internal threaded surface 63. In the configuration shown in FIG. 2a, the piston stem 15 and piston 25 are being displaced in the distal direction and forcing liquid 69 through the central aperture of the cannula 35. As is shown in FIG. 2b, the slide lock 27 is engaging the peripheral locking neck 41, and the slide lock 27 is shown in a position displaced away from the axis of the cannula 35. As can be seen in FIG. 2b, the radial diameter of the larger aperture 71 is larger than the radial extent of the distal end of the needle axial translating structure 37, and that if the slide lock 27 were to shift position bringing flat surface 31 closer to the cannula 35, then the needle axial translating structure 37 would be released.

Referring to FIG. 3b, the slide lock 27 is shown in a position shifted such that, for example, a thumb of the user could engage the flat surface 31, to shift it from the position it assumed in FIG. 2b. Note that the radial diameter of the smaller aperture 73 is now shown and is smaller than the radial extent of the distal end of the needle axial translating structure 37, and that the disk-like flange 43 is now in a position of release.

Referring to FIG. 3a the disposable pre-filled safety syringe is shown in a position which would be achieved after liquid 69 has been expelled from the syringe body 19 through the cannula 35. Once this occurs, the piston 25 is driven distally to the extent that the stopper attachment cone 45 engages the receptacle 68, which locks the stopper attachment cone 45 to the receptacle 68. Next, the slide lock 27 is been shifted to a position which was shown in FIG. 3b. The piston stem 15 is then withdrawn in the proximal direction, pulling both the piston 25 and the needle axial translating structure 37 with it.

FIG. 3a illustrates this action with the piston 25 shown as being withdrawn almost to its most proximal extent. FIG. 4 illustrates the piston 25 after it has indeed been moved to its most proximal extent and has engaged the lip 61. Note that the cannula 35 is within the syringe body 19. The cannula 35 can be pre-stressed with respect to the needle axial translating structure 37 to cause the cannula 35 to be canted to one side once it is withdrawn into the syringe body 19. This would prevent the tip end of cannula 35 from being able to extend back through the opening in the distal head 51. FIG. 4 also shows the distal head 51 and its planar surface 65 and large pitch thread 67 disengaged from the piston 25 and moved out of the vicinity of the flange 17.

This prevents someone from inadvertently pushing forward on the piston 25 which could, if the cannula 35 were not canted enough, extend through the distal opening in the syringe body 19 adjacent the distal head 51. Note that the lip 61 can be made extreme with respect to the diameter of the syringe body 19 to prevent other objects of correspondingly small diameter from being used to push the piston 25 in the distal direction,.

The disposable pre-filled safety syringe of the present invention is then disposed of with the piston stem 15 and the syringe body 19 and the structures engaging it to be disposed of in a mutually detached manner.

While the present invention has been described in terms of a pre-filled safety syringe having a retractable needle, one skilled in the art will realize that the structure and techniques of the present invention can be applied to many similar appliances. The present invention may be applied in any situation where hazardous surfaces are sought to be rapidly and easily protected from harmful contact, and especially in a disposable mechanism.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed is:

1. A syringe comprising:
    a hollow cylindrical syringe body having an open proximal end and an open distal end, a head at said distal end, and a neck extending proximally from said head;
    a slide lock engaging said head and said neck;
    a needle translating structure having a peripheral locking neck selectably engageable by said slide lock;
    a cannula rigidly affixed to said needle translating structure;
    a piston assembly interconnected with said needle translating structure and movable through said syringe body; and
    a flange engaging said syringe body at said proximal end and including a radially inwardly projecting lip which extends radially inward of said syringe body to block said piston assembly from moving proximally out of said open proximal end of said syringe body.

2. The syringe recited in claim 1 wherein said piston assembly comprises:
    an elastomeric piston having a proximal end including an internally threaded surface; and
    a piston stem having a thread engageable to said internally threaded surface of said elastomeric piston.

3. The syringe recited in claim 2 wherein said needle translating structure has a cone extending in the proximal direction, and wherein said elastomeric piston has a receptacle lockably mated to said cone.

4. The syringe recited in claim 3 wherein said cone is axially centered with respect to said needle translating structure and wherein said receptacle is axially centered with respect to said elastomeric piston.

5. The syringe recited in claim 2 wherein said elastomeric piston also has a plurality of ribs extending radially outwardly of said elastomeric piston to sealingly engage the interior of said hollow syringe body.

6. The syringe recited in claim 2 wherein said piston stem also has a thumb plate at the proximal end of said piston stem to facilitate manual movement of said piston stem into and withdrawal from said syringe body.

7. The syringe recited in claim 1 wherein said slide lock defines a distal end having a smaller superposed aperture defined by the partial overlap of a smaller radius circle with a larger radius circle and having a proximal end having a larger superposed aperture defined by the partial overlap of two circles, said larger superposed aperture engaging said neck of said syringe body.

8. The syringe recited in claim 1 wherein said needle translating structure has a longitudinal axis and wherein said cannula is rigidly affixed to said needle translating structure at an angle with respect to said longitudinal axis of said needle translating structure.

9. The syringe of claim 1 wherein said flange engaging said syringe body at said proximal end defines a concentrically smaller diameter portion having a relatively longer axial length and a relatively larger diameter portion having a relatively shorter axial length.

10. The syringe recited in claim 1 wherein said slide lock is shifted relative to said head and said neck of said syringe body to detachably connect said needle translating structure to the open distal end of said syringe body.

11. A syringe comprising:

a hollow cylindrical syringe body having an open proximal end and an open distal end, a head at said distal end, and a neck extending proximally from said head;

a needle translating structure extending through said head;

locking means to detachably connect said needle translating structure to said open distal end of said syringe body;

a cannula rigidly affixed to said needle translating structure;

a piston engaging the interior of said hollow syringe body and translatable axially through said syringe body; and piston stop means, attached to and projecting inwardly of said open proximal end of said syringe body, for preventing said piston from exiting said syringe body at said proximal end of said syringe body.

12. The syringe recited in claim 11 wherein said syringe further comprises a piston stem engaging said piston.

13. The syringe recited in claim 11 wherein said locking means is a slide lock having a distal end having a smaller superposed aperture defined by the partial overlap of a smaller radius circle with a larger radius circle and having a proximal end having a larger superposed aperture defined by the partial overlap of two circles, said proximal and said distal ends of said slide lock at least partially surrounding said head of said syringe body.

14. The syringe recited in claim 13 wherein said slide lock defines a peripherally outwardly disposed curved surface continuous with a peripherally outwardly disposed flat surface.

15. The syringe recited in claim 11 wherein said needle translating structure has a longitudinal axis and wherein said cannula is rigidly affixed to said needle translating structure at an angle with respect to said longitudinal axis of said needle translating structure.

16. The syringe recited in claim 11 wherein said needle translating structure includes a disk-like flange and said syringe further comprising a gasket surrounding said needle translating structure and seated against said disk-like flange.

17. The syringe recited in claim 11 wherein said needle translating structure has a cone extending in the proximal direction, and wherein said piston includes a receptacle lockably mated to said cone.

\* \* \* \* \*